United States Patent [19]
Taylor et al.

[11] 3,970,705
[45] July 20, 1976

[54] PREPARATION OF UNSATURATED ETHERS

[75] Inventors: Brian W. Taylor; Harold E. Swift, both of Gibsonia, Pa.

[73] Assignee: The B. F. Goodrich Company, Akron, Ohio

[22] Filed: Aug. 4, 1975

[21] Appl. No.: 603,147

Related U.S. Application Data

[63] Continuation of Ser. No. 374,690, June 28, 1973, abandoned, which is a continuation-in-part of Ser. No. 228,268, Feb. 22, 1973, abandoned.

[52] U.S. Cl. ..................... 260/614 R; 260/611 R; 260/613 D; 260/613 R
[51] Int. Cl.² .................. C07C 41/06; C07C 41/10
[58] Field of Search ................................ 260/614 R

[56] References Cited
UNITED STATES PATENTS

| | | |
|---|---|---|
| 1,941,108 | 12/1933 | Reppe ............................ 260/614 X |
| 2,042,219 | 5/1936 | Groll et al. ....................... 260/614 X |
| 2,176,055 | 10/1939 | Britton et al. ......................... 260/640 |
| 2,382,031 | 8/1945 | Soday ................................... 260/614 |
| 2,560,350 | 7/1951 | Jelinek ............................. 260/614 X |
| 3,271,461 | 9/1966 | Stephenson ......................... 260/614 |
| 3,487,114 | 12/1969 | Irick et al. ....................... 260/614 X |

*Primary Examiner*—Howard T. Mars
*Attorney, Agent, or Firm*—J. Hughes Powell, Jr.

[57] ABSTRACT

Saturated and/or unsaturated monohydric alcohols are added to allylic halides in the presence of copper (I) halide and a solid organic-insoluble acid acceptor such as MgO to form ethers in which at least one and preferably both of the organic groups attached to the ether oxygen atom contains a single carbon-to-carbon double bond.

3 Claims, No Drawings

PREPARATION OF UNSATURATED ETHERS

RELATED APPLICATION

This is a continuation of application Ser. No. 374,690, filed June 28, 1973, now abandoned which in turn is a continuation-in-part of our earlier application, Ser. No. 228,268, filed Feb. 22, 1973, now abandoned.

BACKGROUND OF THE INVENTION

1. Field of the Invention

The present invention is the method of preparing ethers with unsaturation in one or both of the groups attached to the ether oxygen atom, by the catalyzed reaction of an allylic halide with an alcohol.

Ethers with such unsaturation are useful as, e.g., comonomers in the polymerization of epichlorohydrin and related epoxy monomers, in the preparation of drying oils, and specialty solvents.

2. Description of the Prior Art

Ethers with unsaturation in one or both of the groups attached to oxygen are known in the art. Heretofore, methods for making the di-unsaturated ethers have been commercially unattractive, e.g., by the removal of alcohol from an acetal.

U.S. Pat. No. 1,941,108 discloses a process for making mono-olefinic ethers by reacting a vinyl halide, an alkylidene halide or an alkylene halide with an alcoholate of the aliphatic, cycloaliphatic, aliphatic-aromatic or aromatic series alcohol in the presence of an organic diluent, solvent or suspending agent. A similar process is shown by U.S. Pat. No. 2,042,219 wherein mono- or di-unsaturated ethers are produced by reacting a suitable unsaturated hydrocarbon halide with an alcohol under aqueous alkaline conditions, the examples of the latter showing the use of aqueous sodium or potassium hydroxides and solid calcium oxide in water [Ca(OH)$_2$?].

Similarly, U.S. Pat. No. 2,382,031 describes a method of making the diether of isoprene alcohol starting with an isoprene-containing gas oil stock by first reacting the isoprene with hydrogen chloride to form isoprene monohydrochloride, hydrolyzing the latter with caustic alkali to form isoprene alcohol, and then converting the latter compound to the diisoprene ether by several methods including (a) reacting the alkali metal alcoholate of isoprene alcohol with isoprene monohydrochloride, (b) dehydration of isoprene alcohol with H$_2$SO$_4$, and (c) by reaction of isoprene alcohol with isoprene monohydrochloride in the presence of alkali.

It is also known in the art to make mono-unsaturated ethers by reaction of a diene with a saturated alcohol. However, when attempting to produce the unsaturated ethers of the present invention by reacting dienes with unsaturated alcohols, economically unattractive amounts of the symmetrical ether formed by the reaction of two molecules of the unsaturated alcohol are produced. Attempts to suppress the undesired reaction without deleterious effect on the alcohol-diene addition have been unsuccessful.

It is also known, as in U.S. Pat. No. 3,271,461, to react a diene with a saturated alcohol in the presence of (1) a cuprous halide catalyst and (2) an acid co-catalyst. Such a process is a very slow process requiring reaction times of up to 100 hours as shown in the patent. While such patent indicates that the alcohol ingredient can be unsaturated (but shows no example thereof), it has been found that the method actually is inoperative with unsaturated alcohols. It has been found that, unlike saturated alcohols, the unsaturated alcohol reacts quite readily with any hydrohalogen acid liberated forming water which, in turn, hydrolyzes the copper halide catalyst diactivating same and/or causing separation of an aqueous phase which will contain all the copper catalyst in inactive form and the organic phase contains small amounts of a diether of the unsaturated alcohol. When the process of the patent is carried out with an unsaturated alcohol at the higher temperatures recited therein, the dehydration of the unsaturated alcohol is increased forming sufficient water to cause phase separation. The examples below show the effects.

Thus, the prior art methods for making ethers containing at least one hydrocarbon group containing a carbon-to-carbon double bond have operated under either strongly basic conditions employing alcohol-soluble alkalines or strongly acidic conditions. Contrary to this art, the great value of copper halide catalysts when employing unsaturated alcohols has not been realized.

SUMMARY OF THE INVENTION

It is among the objects of this invention to improve the copper-catalyzed ether forming reaction.

According to this invention, such reaction wherein allylic halides of the class defined below are reacted with a saturated monohydric alcohol or a mono-unsaturated monohydric alcohol of the class defined below in the presence of a dissolved copper I halide catalyst is improved by employing a solid acid-acceptor material insoluble in the reaction medium and which exhibits a sufficiently basic reaction to react with any hydrogen halide liberated during the ether forming reaction. The resulting improved method is capable of forming both symmetrical and unsymmetrical ethers in which each organic group attached to the ether oxygen contains up to a single carbon-to-carbon double bond. Such ethers are formed nearly quantitatively from the starting materials. It appears essential that any hydrogen halide formed in the course of the reaction be neutralized by a solid, insoluble acid-acceptor material in order to prevent dehydration of the alcohol and/or formation of an unwanted symmetrical ether formed from the alcohol ingredient alone.

With a solid, organic-insoluble acid-acceptor which is not soluble in the reaction medium, the reaction medium is neither strongly acidic nor strongly alkaline as has been the case of the reaction media of the prior art.

The solid acid-acceptor material should be insoluble in the reaction medium and preferably should react with hydrogen halides forming halide salts also insoluble in the reaction medium. Such material is selected from the class consisting of the compounds of metals of groups 1b through VIII of the periodic table. Compounds of this class include copper oxide, silver oxide, magnesium oxide, calcium oxide, calcium hydroxide, calcium carbonate, barium oxide, barium carbonate, zinc carbonate, cadmium oxide, lanthanum oxide, zirconium oxide, the tin oxides, the vanadium oxides, antimony oxide, the molybdenum oxides, and many others. From the standpoint of cost, ready-availability and effectiveness the oxides of polyvalent metals selected from the class consisting of the metals of groups 2a and 2b of the periodic table are preferred. Most preferred are the oxides of magnesium, calcium and barium.

The alcohol ingredient employed in the method of this invention may be any selected from the class consisting of the monohydric alcohols of the aliphatic, substituted aliphatic, cycloaliphatic and substituted cycloaliphatic series containing up to one carbon-to-carbon double bond and from 1 to about 20 carbon atoms per molecule. Stated another way, any saturated monohydric alcohol or any monounsaturated monohydric alcohol meeting the above definition can be employed. Illustrative saturated alcohols useful in the invention include methanol, ethanol, propanol, any of the isomeric butanols, any of the pentanols, n-hexanol, 2-ethylhexyl-alcohol, n-decanol, undecanol, octadecanol, cyclohexanol, 2-butyl cyclohexanol, and others. Monounsaturated alcohols useful in the process include allyl alcohol, 4-hydroxy-1-butene, 1-hydroxy-3-butene, 2-hydroxy-4-pentene, 1-hydroxy-4-phenoxy-3-cyclohexene, 1-hydroxy-4-ethyl-3-cyclohexene and others. Preferred alcohols are the monounsaturated monohydric alcohols within the above definition in which a single double bond is present in a vinylidene ($CH_2 = C<$) group and containing from 3 to 8 carbon atoms per molecule, illustrated preferred unsaturated alcohols being allyl alcohol, 1-hydroxy-3-butene, 2-hydroxy-4-pentene, and others. Polyhydric alcohols in the process of this invention are liable to form polyether products of complex structure which are not the subject of this invention.

The allylic halide ingredient of the method of this invention is any compound selected from the class consisting of mono-unsaturated organic halogen-containing compounds containing a single halogen in a position allylic to a carbon-to-carbon double bond, which contains from 3 to about 20 carbon atoms per molecule, and which are devoid of groups containing reactive hydrogen. By "reactive hydrogen" is meant reactive hydrogen atoms such as are present in hydroxyl, amino and mercapto groups. The presence of reactive hydrogen in the structure of the allylic halide may lead to the formation of polyethers and/or to polymeric substances of complex structure neither of which are the subject of this invention. Preferred allylic halides of the structure defined contain from 3 to 8 carbon atoms per molecule and in which the double bond is present in a vinylidene group ($CH_2 = C<$) group.

The carbon chain of both the allylic halide and the alcohol ingredient may contain other chemical groups which are inert during the ether-forming reaction including non-allylic halogen atoms. Similarly, the two ingredients may contain ester, ether, nitro and other groups free of reactive hydrogen.

Any of the halogens including fluorine, chlorine, bromine and iodine, may be present in the allylic halide and copper I halide (or cuprous halide) catalyst ingredients. However, the halogens with an atomic weight above 30 are preferred, with chlorine being most preferred.

Illustrative allylic halides which may be employed in the method of this invention are:

Allyl chloride; 3-chloro-1-butene; 1-chloro-2-butene; 3-bromo-2-methyl-1-butene; 4-iodo-2-hexene; 3-chloro-6-phenyl-1-heptene; 1-bromo-4-ethoxy-2-butene; 3,5-dichloro-1-pentene; 3-chloro-4-ethyl-1-heptene; 3-chloro-1-cyclohexene; 3-chloro-5-methyl-1-cyclohexene; and many others. Most preferred are allyl chloride, 3-chloro-1-butene and 1-chloro-2-butene.

DESCRIPTION OF PREFERRED EMBODIMENTS

The preferred embodiment of the present invention is the method for preparing ethers with a single terminal carbon-to-carbon double bond in each of the two groups attached to the ether oxygen atom, which method comprises reacting in the substantial absence of water and oxygen an allylic halide of the class described with an unsaturated alcohol containing a single carbon-to-carbon double bond, preferably present in a vinylidene $CH_2 = C<$ group, in the presence of (1) a copper I halide catalyst and (2) a solid acid acceptor compound as defined above, and thereafter recovering the product ether by procedures relatively simpler than those employed in the art described above, namely by simple filtration and fractional distillation to recover a relatively pure form of the desired product.

The process of this invention can be carried out at any temperature from about 0° to about 150°C, more preferably between about 25° and about 100°C, and most preferably between about 50° and about 100°C. One of the advantages of the insoluble acid-acceptor ingredient of this invention is that it appears to suppress dehydration of unsaturated alcohols and permits operation of the process at higher temperatures than could otherwise be employed where reaction rates are high. The process can be operated both with and without solvents and/or diluents and, in fact, the use of solvents and diluents are not preferred since their use reduces equipment capacity and increases recovery and purification costs. The allylic halide, the alcohol, the copper catalyst and the solid acid acceptor need only be mixed and stirred together for a short reaction period at a temperature in the range specified. Pressure has little effect on the reaction although it is preferred to operate in closed vessels at a superatmospheric pressure up to about 100 psig in order to exclude moisture and oxygen and maintain the reactants in the liquid state.

When the cuprous halide catalyst ingredient is added to the reaction mixture, it usually dissolves therein forming a homogenous solution in the organic materials. The copper catalyst residue is easily washed out of the product with water. Generally, the catalyst is required only in very small proportions ranging from about 0.1 to about 2%/wt. more preferably between about 0.5 and 1.5%/wt., based on the total weight of reacting ingredients.

The two main ingredients, the allylic halide and alcohol, should be combined in proportions which are near stoichiometric requirements although it is generally preferable to utilize an excess of the generally cheaper alcohol ingredient which is a good solvent for the copper catalyst and the other organic ingredient. An excess of the alcohol drives the reaction towards essentially complete conversion of the generally more expensive allylic halide ingredient, thereby insuring destruction of halogen and simplifying recovery and purification of the ether product since the excess alcohol is easily removed by water-washing and/or distillation.

The acid acceptor should be supplied in a proportion at least equimolar to the allylic halide ingredient. Generally, since the acid acceptor is quite inexpensive, one will want to employ it in at least a small excess of that theoretically required to react with all the halogen content of the allylic halide and copper halide catalyst ingredients in order to insure against free acidity and minimizing contact and agitation requirements. In larger commercial reaction vessels with ordinary stirrers it may be desirable to utilize a significant excess of the acid acceptor in view of the greater difficulty in securing adequate agitation of the mixture of solid and liquid contents.

The following examples are intended as illustrative only of the method of the present invention and the effects of varying the parameters thereof.

EXAMPLE 1

A pressure bottle is cleaned, dried, and purged of oxygen and moisture by sweeping with dry nitrogen. To the bottle are added 0.01 mol copper (I) chloride, 40 milliliters (ml) allyl alcohol, 0.1 mol 3-chloro-1-butene, and 0.15 mol magnesium oxide. The bottle is sealed. The bottle and its contents are heated to 60°C, and held at that temperature while agitating the reactants for 3 hours. The copper chloride appears to dissolve in the organic liquid phase of the reaction mixture. The reaction is cooled to room temperature and the bottle is opened. The contents are filtered to remove solids, the filtrate extracted with n-pentane, and the pentane solution is washed with water prior to drying over anhydrous calcium chloride. The pentane is removed by distillation. Infrared analysis shows that two products have formed; they are identified as 3-allyloxy-1-butene in 90% yield, and 1-allyloxy-2-butene in 10% yield. The 3-chloro-1-butene is found to have been converted quantitatively to the unsaturated ethers. Less than 1% of diallyl ether is found.

EXAMPLE 2

By way of comparison with Example 1, the CuCl/HCl acid co-catalyst system of U.S. Pat. No. 3,271,461 is utilized in an attempt to prepare an ethyl/isoprene ether. The following materials are charged to a reaction bottle in a nitrogen dry box:

| | | |
|---|---|---|
| Cuprous Chloride | 0.40 gm | (4 millimoles*) |
| Ethanol | 30 ml | |
| Ethanol/HCl Sol. | 5 mls | (17.3 millimoles HCl) |
| Isoprene | 25 mls | (250 millimoles) |

*"m.moles" means millimoles
**Prepared by dissolving anhydrous HCl in dry ethanol; contains ca. 14.72%/wt. HCl The bottle is sealed under nitrogen and then agitated at 60°C for 16 hours. On work-up of the contents of the bottle it is found that about 55.6% of the isoprene had been converted the main products being two compounds having the following structures:

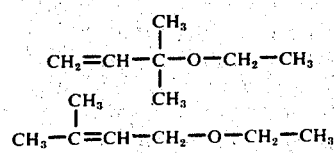

While the conversion is not high, the CuCl/HCl catalyst does convert ethanol and isoprene to ethers.

The above experiment is repeated substituting an unsaturated alcohol, allyl alcohol, for the ethanol of the foregoing experiment. The reaction mixture contained the following materials:

| | |
|---|---|
| Cuprous Chloride | 0.4 gm (4 m.moles) |
| Allyl Alcohol | 40 mls |
| Isoprene | 250 mls |
| Allyl alcohol/HCl Sol.* | 2.0 mls |

*Containing ca 10%/wt. of HCl

After agitation at 60°C in the sealed bottle, analysis of the reaction mixture by gas chromatography indicates that very little of the isoprene (ca less than about 5%) has been converted. The chromatographic analysis showed three minor peaks only one of which could have been assigned to the desired product. The undesired diallyl ether is believed to have been present in the mixture. Other experiments indicate that from about 8% to about 20% or more of the diallyl ether can be formed under such conditions in the absence of a solid acid-acceptor.

EXAMPLE 3

In this example, the process of this invention is employed to prepare an ether from ethanol and 1-chloro-2-butene. The procedure of the foregoing examples is utilized employing the following mixture of materials;

| | | |
|---|---|---|
| Cuprous Chloride | 0.4 gm | |
| 1-chloro-2-butene*- | 2.4 mls. | (30 m.moles) |
| MgO | 1.6 gms | (40 m.moles) |
| Ethanol | 25 mls | |

*Butadiene monohydrochloride

After heating and agitating for only 75 minutes at 60°C., gas chromatographic analysis indicates essentially 100% conversion of the 1-chloro-2-butene to a mixture of addition products which can be considered to be butadiene/ethanol addition products, the products consisting of about 90 mol % of 3-ethoxy-1-butene and about 10 mol % of 1-ethoxy-2-butene.

When the above experiment is repeated utilizing 2.7 gms (30 m.moles) of 1-chloro-2-butene and omitting the MgO, analysis of the mixture after only 30 minutes at 60°C indicates that hydrogen chloride is present. Even after two hours, there is an appreciable proportion (ca at least 20%) of unconverted 1-chloro-2-butene present. Continued heating for a total of 16 hours produced no additional conversion, indicating possibly an equilibrium has been established well below completion of the reaction.

In further contrast, further experiments are carried out as above utilizing ethanol, MgO and either 1-chloro-2-butene or 3-chloro-1-butene, the reaction proceeding to essentially complete conversion of the allylic halide and, moreover, showing a rather surprising result, namely, that the same ether product (3-ethoxy-1-butene) is the main product produced. It may be that the reaction mechanism proceeds through a π - allyl copper complex.

Comparison of the results of Examples 1 and 3 with those of Example 2 shows that the low acid reaction medium of the process of this invention produces, with both unsaturated and unsaturated alcohols, a considerably more vigorous reaction which rapidly proceeds to essential complete conversion of the allylic halide ingredient. Further advantages of the method of this invention will appear in connection with Example 4 below.

EXAMPLE 4

In this example, an attempt is made to convert 3-chloro-1-butene and an unsaturated alcohol, allyl alcohol, to an ether without employing a solid, insoluble acid acceptor material. The procedure is otherwise similar to that of the previous examples. A mixture of 0.4 gm. of cuprous chloride and 20 mls. of allyl alcohol are charged to a pressure bottle under a dry nitrogen atmosphere and the bottle sealed. The mixture is heated at 60°C in a constant temperature water bath for 15 minutes before 3 mls. (30 m. moles) of 3-chloro-1-butene are injected into the sealed bottle and the mixture vigorously shaken until all of the cuprous chloride has dissolved. A sample is taken immediately for analysis, such sample being designated $t_o$ below. The bottle is reimmersed in the bath and removed therefrom periodically to remove additional samples also for analysis by gas chromatography. Such procedure is devised to follow the course of the reaction. The results are as follows:

| Sample(Time) Minutes | % Conversion of Allylic Halide | % diallyl Ether |
| --- | --- | --- |
| $t_o$ | 19.4 | 8.6 |
| 5 | 49.1 | 11.5 |
| 10 | 64.3 | 15.8 |
| 15 | 79.2 | 17.2 |
| 25 | 82.6 | 21.1 |

It is clear from the above, that at a temperature as high as 60°C, a very large proportion of the allyl alcohol is converted to the unwanted diallyl ether and the latter occurrence may be the reason why essentially complete conversion of the allylic halide ingredient is difficult to achieve in the absence of the solid acid acceptor.

When the results of Example 4 are compared to those utilizing allyl alcohol in the procedure of this invention (Examples 1, 3 and 5), it is clear that the solid, insoluble acid acceptor operates to suppress formation of the undesired symmetrical ether formed solely from the unsaturated alcohol ingredient. Apparently, hydrogen chloride liberated in the reaction is removed as fast as formed by reaction with the solid acid acceptor. It may be that hydrogen halide acids can dehydrate the more sensitive unsaturated alcohol.

EXAMPLE 5

In this example, a larger batch of ether is prepared and a more complete work-up and analysis performed on the product. The reaction procedure employed is similar to that of the foregoing examples. The materials utilized are as follows:

| | |
| --- | --- |
| 3-chloro-1-butene | 45 gms (0.5mol) |
| CuCl | 2.0 gms (20 m.moles) |
| MgO | 24 gms (0.6 mols) |
| Allyl alcohol | 200 mls |

The resulting mixture is sealed into a 1-quart pressure bottle under pressure of dry nitrogen. After agitation overnight (ca 16 hours) at room temperature (ca 25°C) the bottle is cooled, opened, the solids filtered off and the filtrate poured into 2 liters of water. After agitating the mixture, 200 ml of n-pentane are added and the mixture agitated again and then allowed to settle. Two layers are formed, one of water and the other an organic layer. The lower water layer is drawn off. The water layer thus separated is shaken with an additional 100 ml. of pentane and the pentane layer separated and combined with the original organic layer. The combined pentane solution is dried over anhydrous calcium chloride and then is distilled. The pentane comes off first after which the temperature of the pot is increased to about 100°C. All of the distillate coming over at pot temperatures of 100°–110°C. is collected and analyzed by gas chromatography. Such distilled crude product has the following analysis:

| | |
| --- | --- |
| Diallyl ether | 0.8% |
| Structure (1) | 86.3% |
| Structure (2) | 12.9% |

STRUCTURE 1

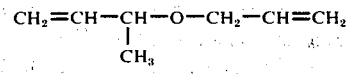

STRUCTURE 2

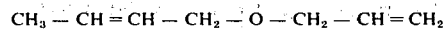

Again one sees that the crude product contains very little diallyl ether. The conversion of 3-chloro-1-butene is essentially complete in the above experiment even though a lower reaction temperature is employed.

In another embodiment carried out with the same raw materials and also carried out at room temperature but omitting the solid acid acceptor, the final product contains approximately 11.2%/wt. of diallyl ether. The latter experiment indicates that the undesirable tendency of highly acidic reaction medium obtained in the absence of the acid-acceptor of increasing the formation of diallyl ether is still present even at the much lower temperature of about 25°C, indicating the acidic co-catalyst method of U.S. Pat. No. 3,271,461 is impractical with unsaturated alcohols at any reasonable reaction temperature.

We claim:

1. In a method of producing unsaturated ethers in which each of the organic groups attached to the ether oxygen atom contain one carbon-to-carbon double bond by the reaction of a mixture of an allylic halide with an unsaturated alcohol, the improvement which comprises dissolving in said mixture a copper I halide and adding to said mixture a solid acid-acceptor material insoluble in said mixture and selected from the class consisting of the oxides of polyvalent metals of groups 2a and 2b of the periodic table and carrying out the said reaction in the absence of solvents and diluents, while maintaining the resulting reaction mixture in liquid form under superatmospheric pressure up to about 100 psig, at a temperature in the range of from about 25° to about 100°C and while substantially excluding moisture and oxygen, said allylic halide ingredient being selected from the class consisting of allyl chloride, 3-chloro-1-butene or 1-chloro-2-butene, said alcohol ingredient being selected from the class consisting of allyl alcohol, 1-hydroxy-3-butene or 2-hydroxy-4-pentene, and said acid-acceptor material is present in a proportion at least equivalent on a molar basis to the said allylic halide ingredient.

2. The method as defined in claim 1 and further characterized by said allylic halide ingredient being 1-chloro-2-butene and said alcohol ingredient being allyl alcohol.

3. A method of claim 2 wherein the oxide of polyvalent metal is the oxide of magnesium, calcium or barium.

\* \* \* \* \*